(12) United States Patent
Molokanova

(10) Patent No.: US 10,688,127 B2
(45) Date of Patent: Jun. 23, 2020

(54) METHODS OF USING GRAPHENE AND GRAPHENE-RELATED MATERIALS FOR MANIPULATION OF CELL MEMBRANE POTENTIAL

(71) Applicant: Elena Molokanova, Encinitas, CA (US)

(72) Inventor: Elena Molokanova, Encinitas, CA (US)

(*) Notice: Subject to any disclaimer, the term of this patent is extended or adjusted under 35 U.S.C. 154(b) by 0 days.

(21) Appl. No.: 16/129,535

(22) Filed: Sep. 12, 2018

(65) Prior Publication Data

US 2019/0015450 A1    Jan. 17, 2019

Related U.S. Application Data

(62) Division of application No. 15/318,974, filed as application No. PCT/US2015/035622 on Jun. 12, 2015, now Pat. No. 10,137,150.

(60) Provisional application No. 61/998,089, filed on Jun. 17, 2014.

(51) Int. Cl.
*A61K 33/44* (2006.01)
*A61N 2/00* (2006.01)
*G01N 33/50* (2006.01)

(52) U.S. Cl.
CPC .............. *A61K 33/44* (2013.01); *A61N 2/002* (2013.01); *G01N 33/5023* (2013.01); *G01N 33/5058* (2013.01)

(58) Field of Classification Search
CPC .. A61K 33/44; G01N 33/5023; G01N 3/5058; A61N 2/002
USPC .................................................. 424/400, 600
See application file for complete search history.

(56) References Cited

U.S. PATENT DOCUMENTS

| 662,997 | A | 12/1900 | Wren |
| 6,629,971 | B2 | 10/2003 | McDaniel |
| 2012/0034622 | A1* | 2/2012 | Ignatius ............... B82Y 5/00 435/7.2 |
| 2012/0272868 | A1* | 11/2012 | Berry ................. B82Y 30/00 106/286.8 |
| 2014/0174927 | A1 | 6/2014 | Bashir et al. |
| 2014/0159181 | A1 | 12/2014 | Kim |
| 2015/0329852 | A1 | 11/2015 | Nolan |

OTHER PUBLICATIONS

Author: Jim Lucas, title:What Is Electromagnetic Radiation? Live Science, nknown author, electromagnetic radiation definition Mar. 13, 2015 (Year: 2015).*
Fitzer, technical status and future prospects of carbon fibres and their application in composites with polymer matrix, Based on papers presented at the International Conference on Carbon Fibre Applications, Sao Jose dos Campos (SP), Brazil, Dec. 5-9, 1983.
Heo et al., "The control of neural cell-to-cell interactions through non-contact electrical field stimulation using graphene electrodes". Biomaterials. Jan. 2011;32(1), pp. 19-27. doi: 10.1016/j.biomaterials. 2010.08.095.
Iancu, "Nanoscience and Nanotechnology" Annuals of the Academy of Romanian Scientists. Series on Science and Technology of Information. ISSN 2068. 1984, vol. 3, No. Feb. 2010, pp. 91-110.
Jiang, "Chemical preparation of graphene-based nanomaterials and their applications in chemical and biological sensors" Small. Sep. 5, 2011;7(17), pp. 2413-2427. Doi: 10.1002/smll.201002352.
Li et al. "Three-dimensional graphene foam as a biocompatible and conductive scaffold for neural stem cells". Sci Rep. 2013;3:1604. doi: 10.1038/srep01604.
Mendes "Cellular nanotechnology: making biological interfaces smarter". Chem Soc Rev. Dec. 21, 2013; 42(24), pp. 9207-9218. Doi: 10.1039/c3cs60198f.
Parlak et al. "On/Off-switchable zipper-like bioelectronics on a graphene interface". Adv Mater. Jan. 22, 2014;26(3), pp. 482-486. doi: 10.1002/adma.201303075.
Sigma-Aldrich, title: quantum dots, product information downloaded from https://www.sigmaaldrich.com/technical-documents/articles/materials-science/nanomaterials/quantom-dots.html on May 23, 2018.
Singh et al. "Carbon nanotubes in hyperthermia therapy". Adv Drug Deliv Rev. Dec. 2013;65(15), pp. 2045-2060. doi: 10.1016/j.addr. 2013.08.001.
USF, title: one-step synthesis of graphene quantum dots, Tech ID #14A053 downloaded from http://www.research.usf.edu/dpl/content/data/PDF/14A053.pdf on May 23, 2018.
Wikipedia, title: Graphene, downloaded from https://en.wikipedia.org/wiki/Graphene on May 23, 2018.
Yang et al. "Nano-graphene in biomedicine: theranostic applications". Chem Soc Rev. Jan. 21, 2013;42(2), pp. 530-547. doi: 10.1039/c2cs35342c.

* cited by examiner

*Primary Examiner* — Yanzhi Zhang
(74) *Attorney, Agent, or Firm* — Knobbe, Martens, Olson & Bear LLP

(57) ABSTRACT

Methods for use of structures based on graphene-related materials are disclosed. These structures can be utilized for manipulating the cell transmembrane potential in various biomedical applications.

14 Claims, 5 Drawing Sheets

METHODS OF USING GRAPHENE AND GRAPHENE-RELATED MATERIALS FOR MANIPULATION OF CELL MEMBRANE POTENTIAL

CROSS-REFERENCE TO RELATED APPLICATIONS

This application is a divisional from U.S. patent application Ser. No. 15/318,974 filed Dec. 14, 2016, which is a U.S. National Stage application of International Application No. PCT/US2015/035622 filed Jun. 12, 2015 which claims priority from U.S. Provisional Application No. 61/998,089 filed Jun. 17, 2014, all of which are incorporated by reference herein in their entirety.

BACKGROUND

Changes in the membrane potential of cells are at the basis of many fundamental physiological processes, including heartbeat, brain function, visual and olfactory transduction, and muscle contraction. Cells are often using the electrical signaling to communicate with each other and to change their behavior according to external clues.

The plasma membrane ensures its structural integrity of a cell, and physically separates intracellular compartments from extracellular surroundings. An electric field (E-field) gradient is present across the cell membrane due to a) substantial differences in ion compositions between intracellular and extracellular compartments, and b) insulating physical properties of phospholipid bilayers comprising the cell membrane. At rest, the inside of cells is more negatively charged than the outside, resulting in the resting membrane potential in the range from −10 to −80 mV in different types of cells. Changes in the membrane potential can be triggered by electrical and/or chemical signals. Specifically, these signals lead to opening of voltage-gated or ligand-gated ion channels, resulting in changes in membrane permeability, redistribution of ions on intracellular and extracellular sides of the plasma membrane, and, finally, changes in the membrane potential.

To control the membrane potential is to control the activation state of a cell. Changes in the membrane potential can lead to a variety of downstream effects, as they are tightly linked to such fundamental functions as cellular excitability, posttranslational modification of proteins by voltage-dependent phosphatases, hormone secretion, ion homeostasis, regulation of protein expression, and cell proliferation. A special situation exists in excitable cells (e.g., neurons or cardiomyocytes (CMs)), where relatively minor changes in the membrane potential can be amplified and result in chain-type activation of multiple ion channel types in a concerted manner, leading to generation of action potential. Even in non-excitable cells, changes in the membrane potential result in changes in electrochemical ion gradients and ion concentrations, which can trigger many seemingly voltage-independent processes.

Numerous in vitro applications that require advanced methods for manipulating the cell membrane potential include fundamental studies of molecular mechanisms in health and disease; functional probing of voltage-sensitive membrane proteins; studies of inter-cellular communications, including synaptic plasticity; cardiology-related projects; visual and olfactory transduction pathways; production and characterization of stem cell-derived cells for cell replacement therapy; activation-dependent maturation and differentiation of stem cell-derived cells; and high throughput screening of drug candidates to assess their potential cardiotoxicity and to support development of personalized medicine.

Novel methods for manipulating the cell membrane potential will also be extremely useful in in vivo applications under circumstances when there is a need to reinforce endogenous activation triggers that become impaired during the disease progression. For example, control over the membrane potential of CMs could help to overcome faulty electrical signaling, and thus, control abnormal heart rhythms. Degeneration of photoreceptors during retinitis pigmentosa or age-related macular degeneration can be compensated via light-driven electrical stimulation of next-in-line intact cells in the retina, potentially leading to restoration of visual perception. Stimulation of neurons can help to compensate for deficits in the neuronal activity in patients with cerebrovascular, neurodegenerative, and psychiatric diseases.

Electrophysiology is the most direct and precise method to control the cell membrane potential. Generally, electrophysiological stimulation by electrode-based techniques (e.g., patch pipettes, multielectrode arrays, or E-field stimulation) exhibits a high degree of control over the cell membrane potential. However, these techniques have significant drawbacks, such as limited, spatial selectivity, invasiveness, low throughput, poor amenability to automation, and general mechanical rigidity of current multi-electrode materials. Furthermore, electrode-based techniques are even less appropriate for studies of contracting CMs due to the damage that a stationary electrode causes in cells experiencing normal physiological movements.

Chemical methods to elicit changes in the membrane potential utilize such approaches as application of a "high $K^+$" extracellular solution or pharmacological ion channel openers. Critical shortcomings of this method include the lack of control of the membrane potential, irreversibility of elicited changes, and low temporal and spatial resolution.

Optical stimulation methods utilize a light beam as an actuator, and thus, could allow long-term non-invasive control over the cell membrane potential. However, existing methods suffer from serious inherent shortcomings. One of the oldest methods in this category is light-triggered "uncaging" of chemically modified signaling molecules such as glutamate, ATP, dopamine, serotonin, cyclic nucleotides. Although the temporal resolution of this method is high, its spatial resolution is limited due to diffusion of "uncaged" molecules from the release site. Additionally, "caged" chemicals show precursor instability, phototoxicity, and require an intense UV illumination. Moreover, the "uncaging" process is irreversible and non-iterative.

The newest and the most promising optical stimulation method, optogenetics, is using genetically encoded transmembrane proteins with either inherent or engineered sensitivity to light. Optogenetics allows controlling the membrane potential in selected subpopulations of cells with unparalleled spatiotemporal precision. However, to provide the light-mediated control, optogenetics requires the expression of exogenous, functionally active proteins that become an integral part of the intracellular machinery. In other words, an investigator has to change physiology of a cell in order to be able to control its behavior, which could be detrimental in studies with stem-cell derived cells. Several technical challenges of optogenetics have already been addressed during a multi-iteration process of protein engineering and extensive tool development over the last several years. However, some problems are inherent to this approach: 1) Optogenetics does not provide physiological stimulation, as ion fluxes and initial membrane potential changes are determined by properties of exogenous proteins rather than endogenous ion channels. 2) High expression levels of light-sensitive proteins are required in order to achieve desired changes of the membrane potential. 3) In many case, addition of endogenous co-factor all-trans-retinal or photoisomerizable compounds is necessary for light-sensitive functioning of optogenetic proteins. 4) Optogenetics is not appropriate for pharmacological profiling of new drugs, because they can directly affect opsins instead or in addition to the target of interest.

Material Science: Photo-induced electrical excitation of neurons has been demonstrated using substrates made of inorganic bulk semiconductors, semiconductor nanoparticles, and organic semiconductor polymers. For example, neurons cultured on silicon wafers can be activated by light, because photo-induced changes in the conductivity of silicon in the presence of a specific voltage applied across the wafer can trigger a capacitive transient in neurons, resulting in their membrane depolarization. Unfortunately, 1) this platform is not transparent and, thus, has limited compatibility with optical detection methods; 2) very expensive and very rigid silicon wafers in a sophisticated controlling device drastically restrict its applicability; 3) the spatial resolution defined by the diameter of the photocurrent spreading is ≥50 μm. Some of these problems were addressed in a substrate where a photosensitive layer was made from a mixture of organic semiconducting polymers. Compared to a silicon-based substrate, this platform does not require any external devices, exhibits low heat dissipation, and has greater potential in terms of flexibility and fabrication simplicity. Its disadvantages include a) incompatibility with optical detection due to low transparency and the visible range excitation; and b) potential miniaturization problems due to mechanical brittleness of polymer layers. Another optical stimulation platform based on semiconductor nanoparticles provided the highest degree of engineering flexibility during its fabrication, but had the limited biocompatibility due to the presence of cadmium-containing components in nanoparticles.

In summary, novel technological tools are needed for remote stimulation of cells. Optimal physiological stimulation tools should be able to change the membrane potential quickly, reversibly, and repeatedly; to control the amplitude, duration, and direction of these changes; to be minimally intrusive and compatible with non-invasive detection methods.

To satisfy these requirements, novel materials with suitable properties can be considered. The family of graphene-based or graphene-related materials (here, the terms "graphene-based" and "graphene-related" are used interchangeably) recently stepped into the spotlight after the 2010 Nobel Prize in Physics, and subsequent explosion in development of numerous applications for these materials in energy, electronics, sensors, light processing, medicine, and environmental fields. Graphene, the "founding" member of this family, is a two-dimensional material made of $sp^2$-hybridized carbon atoms arranged in a hexagonal honeycomb lattice. The extended family of graphene-related materials includes graphene (single- and multi-layered), graphite, polycyclic aromatic hydrocarbons, carbon nanotubes, fullerenes, various graphene nanostructures of different dimensionalities (e.g., graphene nanoparticles, or graphene quantum dots: graphene nanoribbons: graphene nanomeshes; graphene nanodisks; graphene foams; graphene nanopillars), any combinations of other graphene-related materials, substituted graphene-related materials (e.g., the substitution of carbon atoms with N, B, P, S, Si, or others), and graphene-related materials functionalized with reactive functional groups (e.g., carboxyl groups, esters, amides, thiols, hydroxyl groups, diol groups, ketone groups, sulfonate groups, carbonyl groups, aryl groups, epoxy groups, phenol groups, phosphonic acids, amine groups, porphyrin, pyridine, polymers and combinations thereof). Specific examples of graphene-related materials include graphene oxide (GO), graphite oxide, and reduced graphene oxide (rGO).

Graphene and graphene-related materials exhibits extraordinary electronic, mechanical, and optical properties, which could make them invaluable in various biomedical applications, including construction of a biocompatible interface for remote stimulation of cells using electromagnetic radiation. Graphene is highly inert and chemically stable, which results in excellent biocompatibility. Its unique properties include high electrical conductivity, high mobilities of charge carriers, exceptional mechanical properties (e.g., high stiffness, strength, and elasticity), high thermal conductivity, broadband absorption and high transparency over the visible spectrum. Moreover, it is possible to tune electronic and optical properties of graphene for a specific application by pursuing one of many routes such as changing the stacking pattern of graphene sheets, changing the shape of graphene structures, substituting carbon atoms in a graphene lattice, and functionalizing graphene.

Graphene has a zero bandgap, leading to a broadband absorption of incident light with the energy below ~3.5 eV. It means that graphene having the high optical absorption coefficient ($7 \times 10^5$ $cm^{-1}$) can efficiently detect wavelengths of light ranging from 300 to 2500 nm, which includes the entire visible spectrum, infrared and even terahertz regions.

The single layer of graphene is highly transparent with absorption of 2.3% across the visible spectrum and beyond with an absorption peak of ~10% in the ultraviolet. When graphene absorbs photons, it transforms their energy into electrical current by creating photo-generated excitons via photoelectric and/or photo-thermoelectric mechanisms. The photoresponsivity of graphene is somewhat low (<10 $mAW^{-1}$) due to the low optical absorption in monolayer graphene and the short recombination lifetime (on the scale of a picosecond) of the photo-generated carriers, leading to a low internal quantum efficiency of ~6-16%.

GO is a highly oxidized graphene-related material with numerous oxygen-containing functional groups. In contrast to graphene with its zero band gap and high electronic conductivity, GO is a wide-bandgap semiconductor with a bandgap >3.5 eV, and very poor electronic conductivity. The removal of the oxygen-containing functional groups leads to the decrease in the optical bandgap from >3.5 eV to <1 eV, the increase in the optical absorption, and the restoration of the electrical conductivity. This reduction process results in another graphene-related material known as rGO or chemically converted graphene. While graphene and other non-functionalized graphene-related materials (e.g., graphite, carbon nanotubes and fullerenes), are hydrophobic, GO is hydrophilic due to the presence of oxygen-containing functional groups. rGO is intermediate in hydrophilicity because the number of remaining oxygen-containing functional groups in rGO is lower than in the highly oxidized GO.

Among current biomedical applications for graphene and its derivatives are their utilization for tissue engineering, antibacterial treatment, drug and gene delivery, and as contrast agents for bioimaging. For example, incorporation of graphene-related materials as structural elements both for planar or three-dimensional scaffolds for cell cultures greatly enhanced cell adhesion, improved the cell proliferation, accelerated the rate of cell maturation, enhanced the neurite sprouting and outgrowth, and supported the neuronal lineage during the stem cell differentiation. These applications utilized not only pure graphene and its derivatives, but also their hybrid nanocomposites with diverse nanostructures (e.g., semiconductor quantum dots, carbon nanotubes), proteins (e.g., chitosan), polymers (e.g., poly(propylene carbonate)), or other chemical entities (e.g., PEG). It was suggested that positive effects of graphene-related materials on creating favorable cell microenvironment are based on their mechanical properties, micro-scale topographic features, and surface chemistry characteristics.

All existing biomedical applications take advantage of passive steady-state properties of graphene and its derivatives. Currently, there are no applications that utilize external stimuli to actively change physicochemical properties of graphene-related biointerfaces, and subsequently to change the functional state of cells interacting with these interfaces.

SUMMARY OF INVENTION

The use of a biocompatible interface comprising graphene-related materials (G-biointerface) for manipulation of electrical properties of cell membrane both in vitro and in vivo is disclosed.

In one embodiment, a biocompatible interface can comprise one or more structures of graphene-related materials. In another embodiment, graphene-related materials can be doped, functionalized and/or supplemented with one or more chemical entities. In one embodiment, a G-biointerface can be utilized as a stand-alone structure. In other embodiment, G-biointerface structures can be deposited on a substrate.

In a further embodiment, a method of manipulation of the membrane potential via a G-biointerface can comprise the steps of positioning a biological target near a G-biointerface and exposing a G-biointerface to electromagnetic stimuli. In one embodiment, electromagnetic stimuli can be the visible spectrum electromagnetic stimuli.

A method of performing biological assays can comprise the steps of eliciting changes in the membrane potential via a G-biointerface and monitoring resultant changes using one or more detection methods. In one embodiment, detection methods can be optical methods which can result in all-optical assays of probing biological activity when combined with light-activated G-interfaces for manipulating the membrane potential. In one embodiment, detections methods can be genetic methods. In one embodiment, detection methods can be electrophysiological methods.

A method of treating an animal having a medical condition can comprise the steps of administering G-biointerface structures to an animal, and exposing G-biointerfaces to electromagnetic stimuli; wherein the medical condition is any of various pathological conditions, including, but not limited to Alzheimer's disease; Parkinson's disease; amyotrophic lateral sclerosis; Huntington's disease; chemotherapy-induced neuropathy; age-related brain dysfunctions; Down's syndrome; autism spectrum disorders; cerebral palsy; epilepsy and other seizure disorders; affective disorders, depression, TBI/PTSD/CTE (chronic traumatic encephalopathy) and other stress-, traumatic, or blast-related injuries or diseases; schizophrenia and other psychotic disorders; pain, hyperalgesia and disorders of nociception; addictive disorders; neuronal ischemia; neuronal reperfusion injury; neuronal trauma; neuronal hemorrhage; nerve injury; neuronal infection; stroke; cancers; cardiovascular disorders; cardiac arrhythmias; heart failure; cardiomyopathies; rheumatic heart disease; coronary artery disease; congenital heart disease; eye diseases; age-related macular degeneration; retinitis pigmentosa; glaucoma; diabetic retinopathy; calcium homeostasis disorders; glucagonoma; diabetes; hypoglycemia; adrenal disorders; thyroid disorders; growth disorders; metabolic bone disease; sex hormone disorders; sexual dysfunction.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

(B) Summary of cell viability experiments. Data are presented as mean±s.e.m. (n≥100 cells per each experimental condition).

Figure 9:
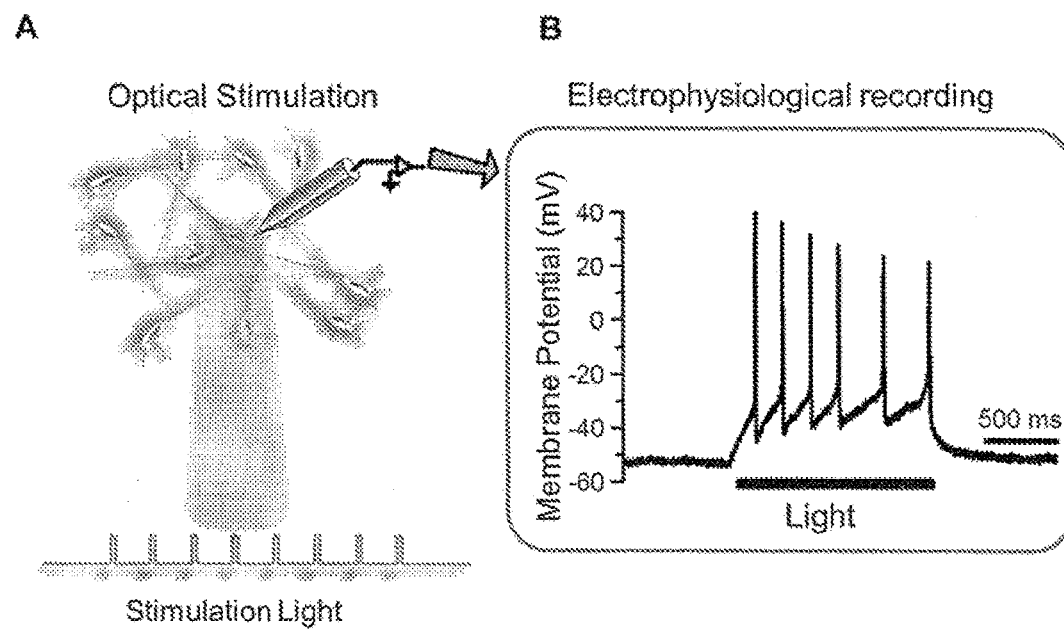

FIG. 9 shows effects of light illumination on the membrane potential of neurons cultured on rGO-coated glass coverslips. (A) Experimental scheme: activation of neurons using light, and monitoring ensuing electrical activity using electrophysiological methods. (B) Light-triggered action potentials in neurons on rGO-coated glass coverslips.

Figure 10:
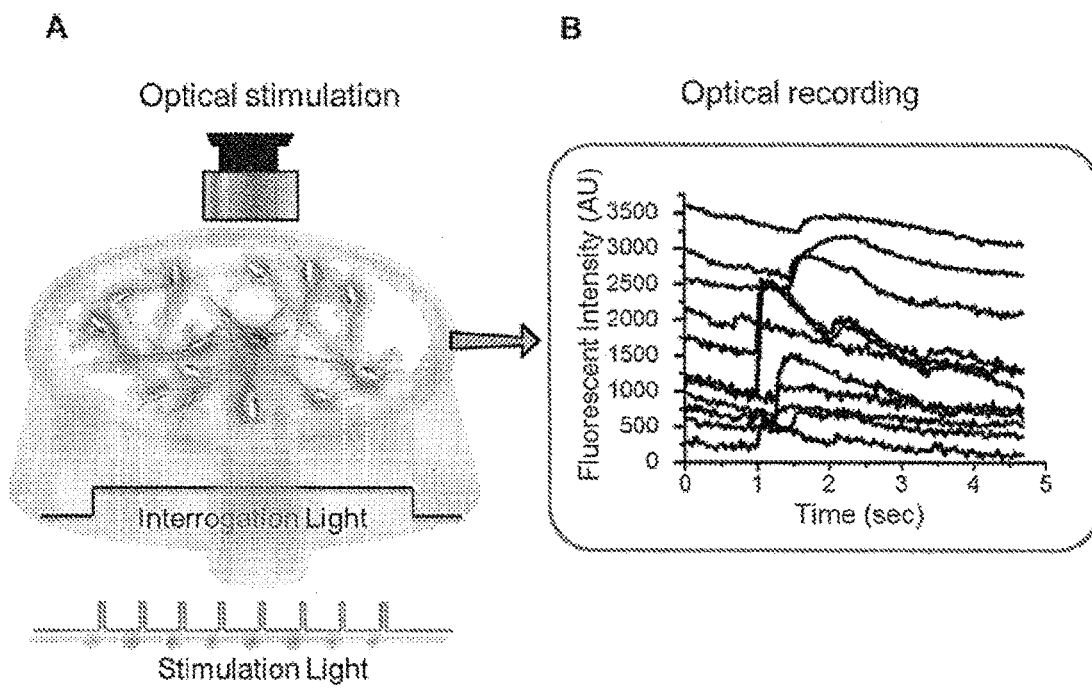

FIG. 10 shows light-triggered effects on distribution of intracellular calcium ions in neurons cultured on rGO-coated glass coverslips. (A) Experimental scheme: activation of neurons using light, and monitoring ensuing changes in intracellular calcium concentrations using optical methods. (B) Individual traces of light-triggered changes in intracellular calcium in multiple neurons cultured on rGO-coated coverslips and labeled with Fluo4, a fluorescent calcium indicator.

DETAILED DESCRIPTION

This disclosure is not limited to the particular systems, devices and methods described, as these may vary. The terminology used in the description is for the purpose of describing the particular versions or embodiments only, and is not intended to limit its scope.

This disclosure presents, among other things, nanostructured biocompatible switchable interfaces based on graphene-related materials, methods of preparing such biointerfaces, methods of utilizing such biointerfaces for production, interrogation, and characterization of cells, methods of utilizing such biointerfaces for pharmacological profiling cells and chemical entities, and well as methods of treating an animal having a medical condition using such biointerfaces.

Figure 1:
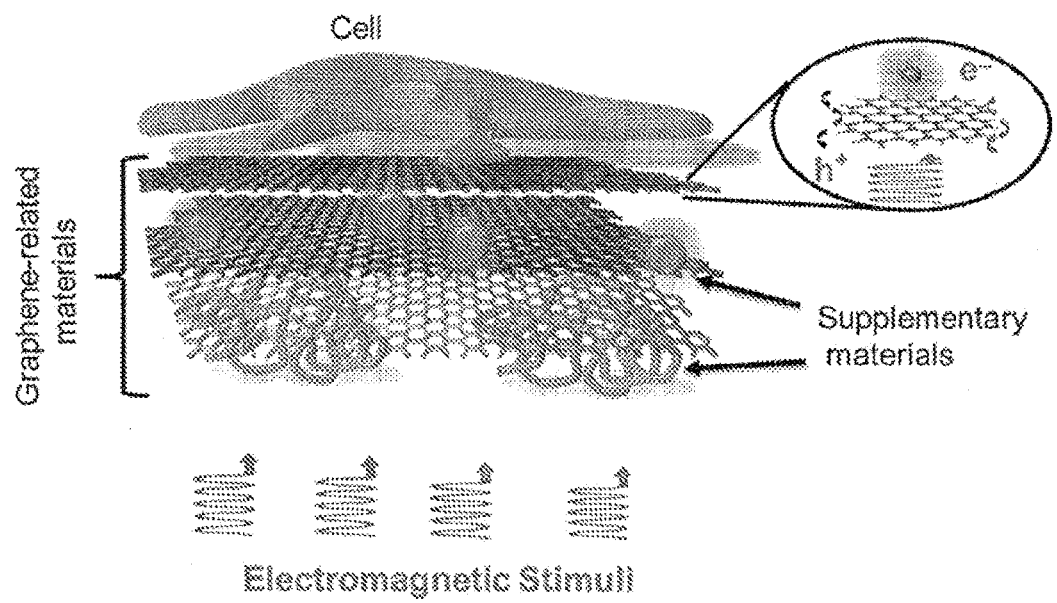
FIG. 1 shows the general strategy of utilizing graphene and graphene-related materials in a biocompatible optoelectronic interface to implement remote stimulation of cells using electromagnetic stimuli.

A general design strategy is based on the following chain of events shown in FIG. 1. 1) During the exposure to electromagnetic stimuli, a graphene-related material absorbs its energy, resulting in generation of excitons, which subsequently dissociate into electrons and holes. 2) Due to the capacitive coupling effect between the cell membrane and the surface of graphene-related materials, photogenerated free charge carriers (e.g., electrons) from the G-biointerface displace cations near the graphene/cell membrane interface. 3) Such re-distribution of charges right outside the cell membrane triggers changes in the cell membrane potential. Large interfacial capacitance of the G-biointerface offers an effective capacitive stimulation. Thus, the interaction of the external light-generated E-field near the G-biointerface and the transmembrane E-field gradient leads to non-invasive remote stimulation of cells.

Graphene-related materials in a G-biointerface can be generally any material that originated from graphene or can be converted to graphene using various methods of fabrication, functionalization, or substitution. The family of graphene-related materials is comprising graphite, graphene, polycyclic aromatic hydrocarbons, substituted graphene-related materials (where some carbon atoms are substituted with such atoms as N, B, P, S, Si, or others), and graphene-related materials functionalized with such functional groups as carboxyl groups, esters, amides, thiols, hydroxyl groups, diol groups, ketone groups, sulfonate groups, carbonyl groups, aryl groups, epoxy groups, phenol groups, phosphonic acids, amine groups, porphyrin, pyridine, polymers, and combinations thereof. An example of functionalized graphene is GO that contains a number of oxygen-containing functional groups. Another example of functionalized graphene is rGO, produced by removal of at least some oxygen-containing functional groups from GO.

Graphene-related materials can be of any dimensionality. In case of graphene, the examples of zero-dimensional nanostructures comprise graphene nanoparticles or graphene quantum dots; the examples of one-dimensional nanostructures are graphene nanoribbons; the examples of two-dimensional nanostructures are graphene sheets, and graphene nanomeshes; the examples of three-dimensional nanostructures are graphite, a stack of graphene sheets; carbon nanotubes, rolled-up sheet(s) of graphene; fullerenes, wrapped-up sheets of graphene; graphene foam; and graphene nanopillars.

Any graphene-related material incorporated into a G-biointerface can be used alone or be a part of a hybrid combination of different numbers of layers of various graphene-related materials of different dimensionality.

Graphene-related materials can be combined with various supplementary materials in order to engineer specific properties in a G-biointerface. Such properties might include the increased absorption efficiency, the desired spectral activation profile, p- or n-type functionality, the speed of switch on-off, processability, durability, compatibility, electrical conductivity, possible chemical functionalization for creating specific biointerfaces, and a three-dimensional configuration. Examples of supplementary materials can include structures made of metal (e.g., gold, silver, iron, iron oxide, titanium dioxide, lanthanide oxide, transition metal, and transition metal oxide), graphene-like materials (e.g., molybdenum disulfide, tungsten disulfide, niobium diselenide, and boron nitride), semiconductor, silica, polymers, or combinations thereof.

Graphene-related materials can be combined with polymers, including, but not limited to, the naturally occurring components of extracellular matrix (e.g., collagen, fibronectin, and laminin) or synthetic polymers (e.g., polyaniline, polypyrrole, and polythiophene).

Graphene-related materials can be used as stand-alone structures without any external structural support, or directly deposited on a substrate. They can also be combined with other materials that can provide independent structural support. Specific spatial configurations of a G-biointerface can be achieved both by exploiting inherent dimensionality of various graphene-related materials and by incorporating appropriate supplementary materials.

External dimensions of a G-biointerface in the X-Y plane can range from nano dimensions (e.g., one nano-sized graphene flake) to macro dimensions limited only by manufacturing capabilities. The minimal dimensions in the X-Y plane are 1 nm by 1 nm. External dimensions along the Z-axis depend on the number of layers of graphene-related materials incorporated into a G-biointerface. The minimal dimension along the Z-axis is defined by the thickness of a non-functionalized graphene monolayer, 0.34 nm.

The target can be one or more intact cells, one or more cellular fractions, or one or more artificial membrane structures. Examples of cellular fractions include any luminal organelles such as nucleus, ribosomes, mitochondria, endoplasmic reticulum, Golgi apparatus, vacuoles, synaptic vesicles and lysosomes. Examples of artificial membrane structures include phospholipid micelles, micro- and nano-capsules, and semi-liquid films on supportive structures.

The one or more cells can generally be any type of cells which have a membrane and membrane potential. For example, the cells can be bacterial (Gram-positive or Gram-negative), eucaryotic, procaryotic, fungal, insect, avian, reptilian, oocyte, fly, zebrafish, fish, nematode, amphibian, or mammalian cells. The methods can also be used on non-cell materials such as artificial membranes, liposomes, and phospholipid bilayers. Examples of primary mammalian cells comprise human, mouse, rat, dog, cat, bear, moose, cow, horse, pig, or Chinese hamster ovary ("CHO") cells. Other examples of types of cells comprise immune system cells (e.g., B-cells, T-cells), oocytes, red blood cells, white blood cells, neurons, CMs, epithelial, glia, fibroblast, stem cells, cancer cells, secretory cells, and immortalized cells.

In order to be activated via G-biointerfaces, cells have to contact or to be positioned in the close proximity to the surface of graphene-related materials. To achieve such positioning, either cells can be added to G-biointerfaces, or G-biointerfaces can be added to cells.

After cells are properly positioned, G-biointerfaces have to be exposed to electromagnetic stimuli, including, but not limited to, the visible spectrum, the radio frequency spectrum, infrared, microwave, terahertz frequencies, or combinations thereof. For example, exposure of G-biointerfaces to electromagnetic waves of the visible spectrum (i.e., light) can be performed by essentially any illumination method, including, but not limited to, laser, mercury lamp, xenon lamp, halogen lamp illumination, or LED illumination.

Stimulation of cells via a G-biointerface can be combined with other means of stimulation, including, but not limited to, electrical stimulation, magnetic stimulation, chemical stimulation, biological stimulation, or combinations thereof.

G-biointerfaces can be used for studies of processes underlying cellular differentiation, migration, proliferation, and excitation-neurogenesis coupling to guide activity-dependent maturation and differentiation of stem cell-derived neurons. In other embodiments, G-biointerfaces can be utilized for production of stem cell-derived cells of a specified degree of maturity. Such stem-derived cells can be patient-specific cells. Stem cell types include embryonic stem cells, adult stem cells, and iPSCs. Examples of cells include, but not limited to, neurons, CMs, photoreceptors, fibroblasts, endothelial cells, pancreatic cells, muscle cells, secretory cells, adipose cells, mesenchymal stem cells, and bone forming stem cells.

G-biointerfaces can also be utilized to benefit neuroregeneration studies by promoting functional recovery after nerve injury by relying on activation-stimulated acceleration of axon outgrowth; and development of neuroprosthetics via integration with neuronal networks for treatment of neural disorders that increasingly depend on electrical stimulation techniques.

Remote stimulation of cells via a G-biointerface can be combined with optical methods for monitoring of cellular activity. Optical output signals can be acquired using brightfield and/or fluorescent light microscopy, and be a result of either label-free experiments or fluorescent labeling of cells. Fluorescent dyes and/or fluorescent proteins can be used for real-time imaging of various events in light-activated live cells, such as changes in intracellular calcium using $Ca^{2+}$-sensitive fluorescent indicators or changes in the membrane potential using voltage-sensitive fluorescent probes. Alternatively, optical assays of G-biointerface-stimulated cells can be the end-point assays where fixed cells are analyzed via immunohistochemical methods. Optical signals can generally be monitored using any suitable light-measuring or light-accumulating instrumentation. Examples of such instrumentation include a photo camera, a digital camera, a CCD camera, a CMOS camera, a video device, CIT imaging, any digital camera mounted on a microscope, a photomultiplier, a fluorometer, a luminometer, a spectrophotometer, and even the human eye.

Remote stimulation of cells via a G-biointerface can be combined with electrical recordings of cellular activity, including, but not limited to, patch clamp techniques, planar electrophysiological systems, microelectrode arrays, field transistors, and carbon nanotubes.

G-biointerfaces can be utilized for bidirectional communication with cells, when, in addition to providing stimulation of cells, a biointerface can be simultaneously used to record cellular activity using either imaging or electrical modality, or combinations of thereof.

Remote stimulation of cells via a G-biointerface can be combined with their subsequent genetic analysis, including but not limited to, PCR, RT-PCR, DNA sequencing, next generation sequencing, DNA microarrays, karyotyping, fluorescence in situ hybridization, calorimetric in situ hybridization, or combinations thereof.

Cellular stimulation via G-biointerfaces can enable monitoring of the functional activity of cells during many studies, comprising a) studies of synaptic plasticity in neuronal networks; b) studies of mechanisms underlying sensory and motor impairments manifested in numerous neurological disorders such as Parkinson's disease, Alzheimer's disease, autism, and amyotrophic lateral sclerosis; c) cardiac studies; d) studies of pancreatic disorders.

G-biointerfaces can be utilized for pharmacological profiling of cells. In this case, benchmark compounds are tested on cells with an unknown genetic make-up, while the cell membrane potential is controlled by electromagnetic radiation of G-biointerfaces, and cellular responses are monitored using any available detection method.

G-biointerfaces can be utilized for drug discovery screening applications, namely the pharmacological characterization of novel chemical entities. In this case, well-characterized cells in different activation states controlled by a G-biointerface are exposed to novel chemical entities, and cellular responses are monitored using any available detection method. Importantly, G-biointerfaces can streamline the development of efficient use-dependent and activity-dependent drugs by providing control over the membrane potential of cells during the drug screening, and thus, be beneficial for characterization of both on-target and off-target effects, as well as detection of the potential toxicity of novel compounds in various cell types in various activation states.

G-biointerfaces can be utilized for treating of an animal having a medical condition. Changes in the cell membrane potential triggered by electromagnetic radiation of G-biointerfaces that are positioned in the close proximity to the affected cells and regions can help to overcome the consequences of reduced or eliminated activity of cells during the disease progression. Examples of diseases that can be treated by G-biointerfaces include, but not limited to, heart arrhythmias, impairments after cardiac infraction, neurodegenerative/neurological disorders, various ophthalmological disorders, and endocrine disorders.

EXAMPLES

All of the compositions and/or methods and/or processes disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and/or processes and in the steps or in the sequence of steps of the methods described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope and concept of the invention.

Example 1: Graphene-Related Materials

Graphene was synthesized on 25-μm-thick copper foils (Alpha Aesar, 13382, 99.8%) with the dimensions of 10 cm×11 cm. Prior to the growth of graphene, the copper foils were cleaned by the following procedure: soaking in a shallow acetone bath, mechanical cleaning in acetone, transferring into a similar bath filled with isopropyl alcohol (IPA), mechanical cleaning in IPA, drying in a stream of compressed air, electropolishing, rinsing with DI water and IPA, and blow-drying under a stream of compressed air. Atmospheric-pressure CVD graphene synthesis was performed in a quartz tube furnace (MTI OTF-1200X-HVC-UL) with the following tube dimensions: d=7.6 cm, l=100 cm.

In our experiments, we used graphene oxide (e.g., from Graphenea Inc.) and reduced graphene oxide that was produced by either chemical reduction (e.g., using hydrazine hydrate, sodium borohydride, or L-ascorbic acid) or thermal reduction of oxidized graphene-related materials. In some cases, the chemical reduction was followed by the thermal reduction.

An typical experiment to produce rGO by the chemical reduction included the addition of 1 mL of hydrazine hydrate to 100 mL of sonicated aqueous GO solution (1 mg/mL), followed by 1-hour incubation of the resulting mixture at 95° C., and subsequent filtration.

Another typical experiment to produce rGO by the chemical reduction included the addition of 100 mg of L-ascorbic acid to 100 mL of sonicated aqueous GO solution (1 mg/mL) at room temperature, followed by vigorous stirring for 48 hours, and centrifugation.

Example 2: Manufacturing of G-Biointerfaces

After glass coverslips (VWR) were cleaned using the Triton X-100 solution for 2 hours, they were thoroughly washed in ethanol and left to dry for 2 hours under the UV light.

To initiate transferring of graphene onto glass coverslips, the copper foil bearing a film of CVD-grown graphene was first spin-coated with a 2.5% w/w solution of Poly(methylmethacrylate) (PMMA) in toluene at 4000 rpm for 60 s. After spin-coating, the exposed graphene on the side of the copper foil opposite the PMMA was etched using an oxygen plasma cleaner (30 s, 30 W, 200 mtorr oxygen pressure). Next, the PMMA/graphene coated copper foil was floated in a bath of 1M iron(III) chloride ($FeCl_3$) for 30 min in order to etch the copper. Then the free-floating PMMA-supported graphene was transferred three times into DI water baths, and then placed onto coverslips by "scooping" the freestanding film out of the DI water bath. After drying at room temperature for 2 hours, the coverslips were placed into an acetone bath overnight to remove the PMMA. Next, the coverslips were rinsed in IPA and dried in compressed air.

In a typical experiment, rGO produced by the chemical reduction of GO was placed on glass coverslips by droplet deposition (10 μL per 12-mm coverslip). Next, rGO-covered coverslips were air-dried for 30 min, and then placed in the UV cell culture hood for sterilization overnight. Alternatively, we produced rGO-coated coverslips by a) depositing GO droplets on glass coverslips as described above, and then b) conducting the thermal reduction of GO directly on glass coverslips by placing them on the stage of the oven (T=200° C.) for 5 min.

To manufacture an rGO-coated 96-well microtiter plate, we deposited 20 mL of 0.1 mg/mL rGO solution that was prepared by the chemical reduction using L-ascorbic acid into each well of a standard 96-well microplate (Thermo-Fisher Scientific). Subsequently, rGO-coated plate was dried and sterilized in the UV cell culture hood overnight.

Example 3: Cell Culture Procedures iPSCs were generated by four-factor reprogramming and differentiated to NPCs. Then NPC cultures were placed on plastic dishes coated with 20 μg/ml poly-L-ornithine overnight (Sigma) followed by 5 μg/ml laminin (Sigma) for at least 2 hours inside incubator or directly on graphene-coated glass coverslips that were further coated with 100 μg/ml poly-L-ornithine followed by 10 μg/ml laminin. NPCs were maintained in NPC base media containing DMEM-F12+ Glutamax (Life Technologies) supplemented with N2 (Life Technologies), B27 (Life Technologies), Pen/Strep and 20 ng/ml fibroblast growth factor (FGF) (Millipore). Media was changed every 2 or 3 days. Once NSCs reached confluency, FGF was withdrawn from the media and maintained for 5 weeks changing media twice per week. After 3-week differentiation neurons were FACS-purified using a cell surface-antigen signature: differentiated neurons were detached using a 1:1 mixture Accutase/Accumax (Innovative Cell Technologies), and stained with CD184, CD44, and CD24 antibodies (BD Biosciences). Neurons negatively stained for CD184 and CD44 and positively stained for CD24 were selected and plated on poly-ornithine/laminin treated graphene-coated coverslips in NPC base media supplemented, with 0.5 mM dbCAMP (Sigma), 20 ng/mL BDNF and 20 ng/mL GDNF (Peprotech).

iCell CMs (Cellular Dynamics International) were thawed per the manufacturer's instructions. 25 μL of the cell suspension (160,000 cells/mL) was added to a gelatin-coated 384-well plate. The cells were then left undisturbed for 48 hours at 37° C. with 5% $CO_2$. After 48 hours, 75 μL of chemically defined medium (CDM) was added to each well for a total of 100 μL, and then the half of the volume was changed every other day. When after 10-14 days in culture CMs began their spontaneous contractions, they were lifted with trypsin and re-plated at a density of 500,000 cells per a 12-mm coverslip. CMs were cultured on coverslips for 2-3 weeks prior to experiments.

Example 4: Biocompatibility of CMs and G-Biointerfaces

Figure 2:
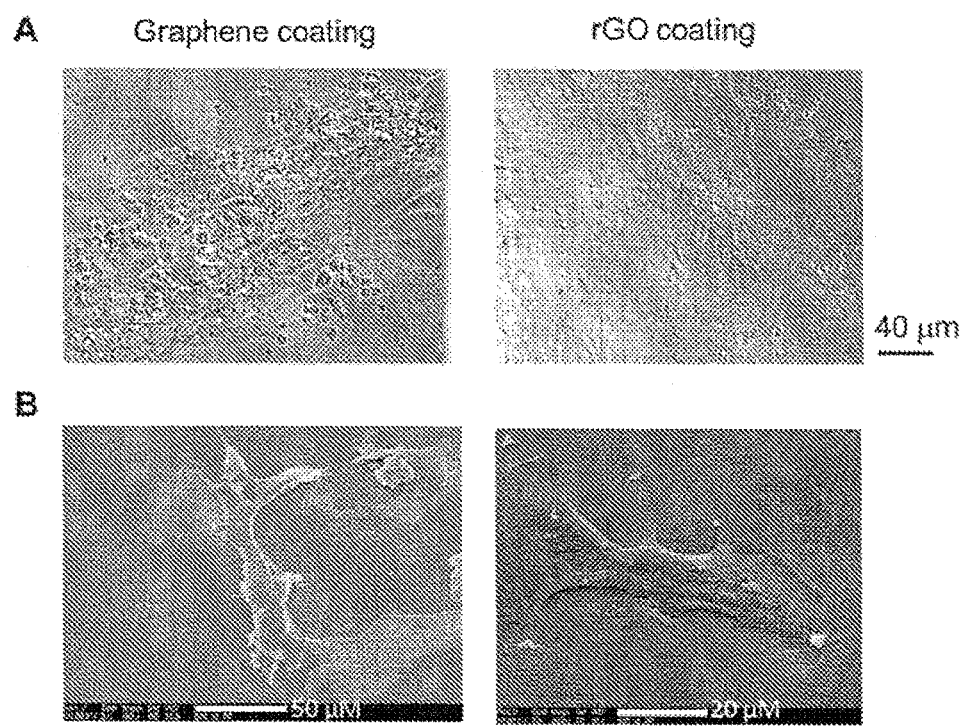
FIG. 2 shows brightfield light microscopy (A) and scanning electron microscopy (B) images of CMs on glass coverslips coated with graphene (left) and rGO (right).

For biocompatibility assessment, we compared morphology, the cell density, and the membrane integrity of cells cultured on glass coverslips with and without coating with graphene-related materials. Brightfield light microscopy images show that CMs exhibit normal morphology when cultured on glass coverslips coated with graphene and rGO (FIG. 2A). To gain additional insight, we followed up with scanning electron microscopy (SEM) experiments. For these experiments, CMs were washed with 0.1 M phosphate buffer (pH 7.4), fixed with 4% formaldehyde solution for 2 hours at room temperature, and washed with the same buffer three times for 5 min each. Following dehydration with graded series of alcohol (50% ethanol—10 min, 70% ethanol—10 min, 80% ethanol—10 min, 95% ethanol—2 changes in 10 min, 100% ethanol—3 changes in 15 min), all samples were freeze dried in a vacuum chamber, and coated with sputtered iridium. We acquired scanning electron microscopy images on the XL30 ESEM-FEG (FEI) at the working distance of 10 mm while using the 10 kV energy beam. SEM images show that CMs are successfully interfacing both with graphene- and rGO-coated glass substrates (FIG. 2B).

Figure 3:
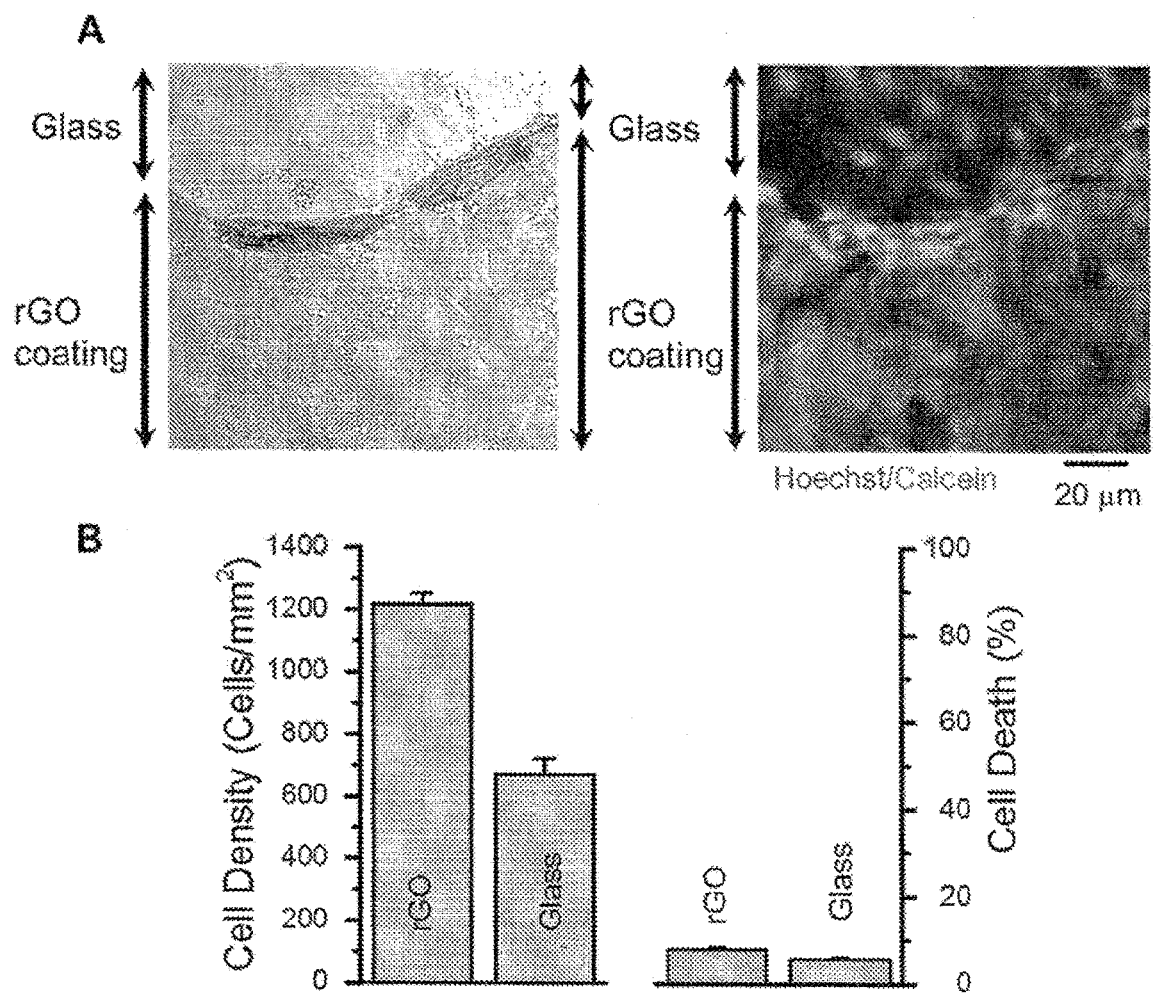
FIG. 3 shows high biocompatibility of rGO-based substrates. Long-term culture of CMs in brightfield (left) and fluorescent (right) light microscopy images of CMs cultured on a heterogeneous substrate as marked (the upper part is the glass, and the lower part is the rGO-coated surface). CMs are labeled with nuclear dye Hoechst (blue) and cytoplasmic dye Calcein (green). (B) Evaluation of cell viability via assessment of the normalized cell density (left) and the membrane integrity (right) for CMs cultured on glass vs. rGO-coated surfaces. The cell density was calculated as the number of cells in the field of view normalized to the control value for cells cultured on glass coverslips. The membranes integrity value was presented as the percentage of cells that exhibited a fluorescent signal after being stained with Calcein-AM and Ethidium homodimer-1 (EchD-1). Data are presented as mean±s.e.m. (n≥100 cells per each condition).

To evaluate the cell density, we calculated the number of cells in a pre-defined area using bright field light microscopy images (FIG. 3A). We determined that CMs prefer the surface coated with graphene and rGO. FIG. 3B (left) shows that the cell density was significantly higher on rGO-coated glass coverslips than on "naked" glass coverslips.

To evaluate the cell viability, we used the LIVE/DEAD® Viability/Cytotoxicity Kit (Life Technologies) that contains membrane-permeable calcein-AM and membrane impermeable Ethidium homodimer-1 (EthD-1). When stained with this kit, live cells with intact cell membranes and high levels of enzymatic activity appear green due to enzymatic conversion of non-fluorescent calcein-AM into green calcein and rejection of EthD-1. In contrast, EthD-1 only enters dead cells with compromised membrane and produces red fluorescent signal upon binding to nucleic acids. Images of labeled cells were randomly taken using the Olympus IX71 fluorescent microscope equipped with standard filters (fluorescein (for calcein), rhodamine (for EthD-1), and DAPI (for Hoechst)), and a QIClick CCD camera (QImaging Inc.). The data were analyzed using ImageJ image analysis software. The cell death was calculated as the percentage ratio of the number of EthD-1-positive cells divided by the sum of the numbers of EthD-1-positive and calcein-positive cells. We determined that the membrane integrity was not statistically different in cells cultured on coated vs. "naked" substrates (FIG. 3B, right).

To test whether culturing CMs on G-biointerfaces is beneficial for their functional activity, we employed brightfield light microscopy to monitor spontaneous contractions of CMs using a label-free approach. To detect the conformational changes occurring in CMs during their contractions, we selected regions of interest (ROIs) right outside the edges of CMs to ensure that the light intensity inside ROIs will change as a result of spontaneous contractions. The frequency was quantified by calculating the contraction number per 1 sec. We found that the frequency of contractions of CMs was higher when cells were cultured on G-biointerfaces.

Example 5: G-Biointerfaces and Light-Triggered Effects in CMs

Figure 4:
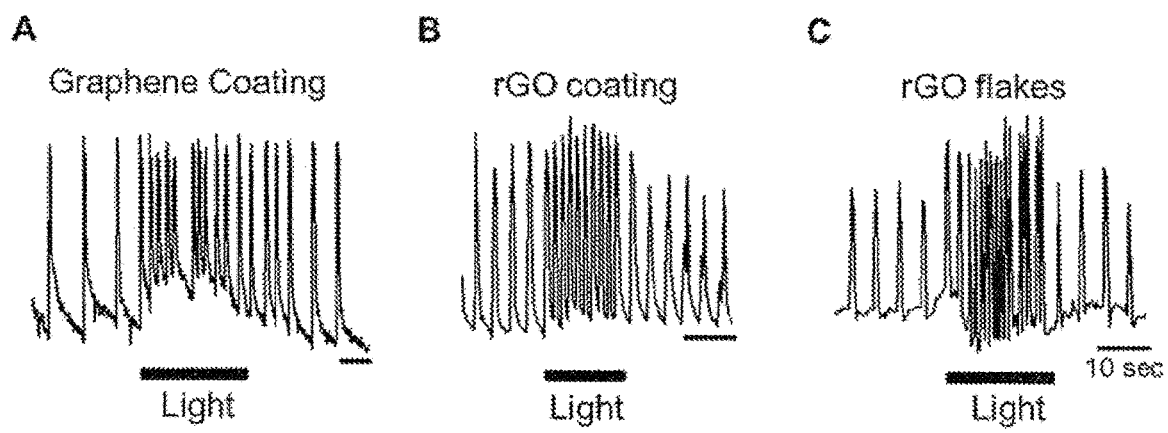
FIG. 4 shows effects of light illumination (blue bars) on the frequency of spontaneous contractions in CMs under the different experimental conditions: (A) long-term culture of CMs on graphene-coated glass coverslips, (B) long-term culture of CMs on rGO-coated glass coverslips, (C) short-term interfacing of rGO flakes with CMs cultured on "naked" glass coverslips. Brightfield microscopy images were used to create the representative traces that reflect changes in the optical density near the cell's edges as a result of contractions of CMs.

Using the label-free approach described in Example 4, we studied the effects of light illumination of G-biointerfaces on spontaneous contractions of CMs in two experimental configurations: a) "long-term" (or chronic) interfacing when CMs were cultured on rGO-coated glass coverslips for 2-3 weeks, and b) "short-term" (or acute) interfacing when rGO flakes were deposited 10 min before experiments directly on CMs cultured on control (e.g., non-coated) coverslips. We found that light illumination resulted in the increase of the contraction frequency of CMs both in chronic (FIG. 4A, B) and acute (FIG. 4C) experimental configurations.

Figure 5:
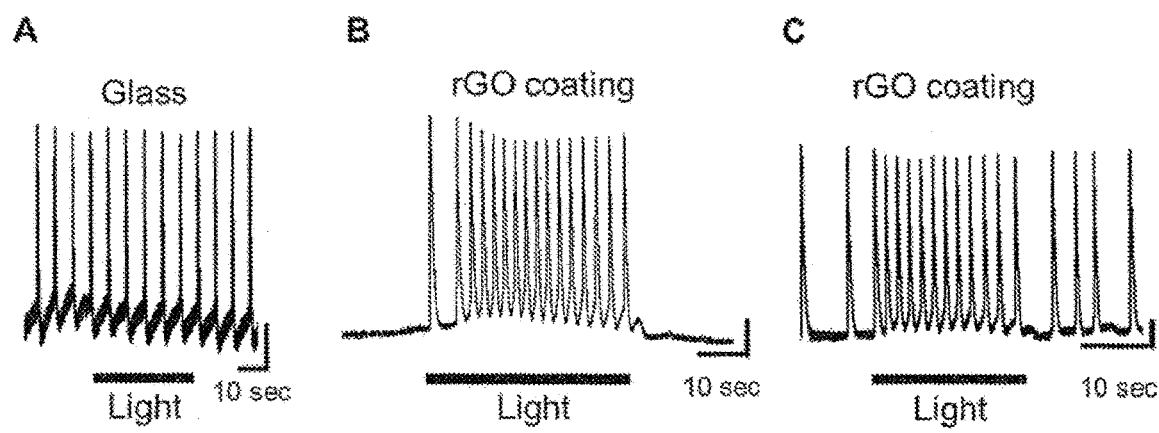
FIG. 5 shows effects of light illumination on action potentials of CMs cultured on glass coverslips (A) and rGO-coated glass coverslips (B, C). Vertical bar, 10 mV.

Using the electrophysiological approach, we monitored light-triggered changes in the membrane potential of cells cultured on the surface of glass coverslips coated with graphene-related materials. In a typical experiment, rGO-coated coverslips were placed in an experimental chamber filled with an electrophysiological extracellular solution consisting of (in mM) NaCl, 135; KCl, 2.5; $CaCl_2$, 2; $NaHCO_3$, 1; $Na_2HPO_4$, 0.34; $KH_2PO_4$, 0.44; glucose, 20; HEPES, 10; and glycine, 0.01 (pH 7.4). Patch pipettes with a final tip resistance of 3-6 MΩ were filled with a solution consisting of (in mM) CsCl, 120; tetraethylammonium chloride, 20; HEPES, 10; EGTA, 2.25; $CaCl_2$, 1; $MgCl_2$, 2 (pH 7.4). All recordings were acquired using a Digidata 1322 interface, an Axopatch 200B amplifier, and pClamp software (Molecular Devices Corp.). We determined that light illumination did not affect CMs cultured on "naked" coverslips (FIG. 5A), but did trigger membrane depolarization in CMs on rGO-coated coverslips, leading to the launch of the train of action potentials (FIG. 5B) or the increase in frequency of action potential generation (FIG. 5C).

Figure 6:
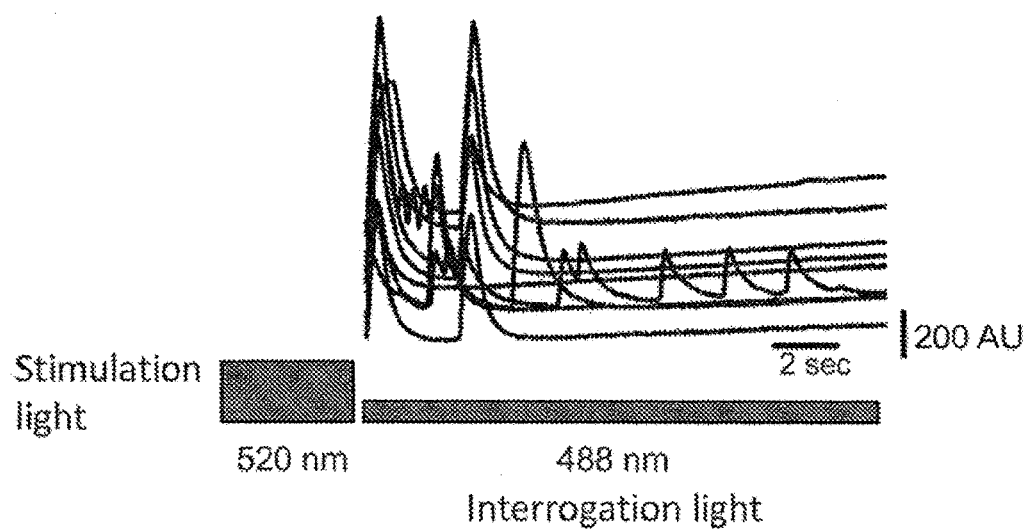
FIG. 6 shows the individual traces of light-triggered changes in intracellular calcium concentration in multiple CMs cultured on rGO-coated glass coverslips and labeled with Fluo4, a fluorescent calcium-sensitive indicator.

An all-optical assay combines light-triggered activation of cells (e.g., via a G-biointerface) and optical methods of monitoring of cellular activity (e.g., using fluorescent biosensors). In a typical experiment, we loaded CMs with either 5 μM Fluo-4 AM, a calcium-sensitive fluorescent indicator (Thermo Fisher Scientific) or 2 μM $VF_{1.2}$, a voltage-sensitive dye, for 45 minutes in the $CO_2$ incubator in the loading buffer (132 mM NaCl; 4.2 mM KCl; 1.8 mM $CaCl_2$, 5 mM D-glucose, 10 mM HEPES; adjusted to pH 7.4). To perform an all-optical assay, we used a brief pulse of high-intensity light at 520 nm to activate a G-biointerface, and continuous illumination with low-intensity light at 480 nm to excite fluorescent dyes. Imaging experiments were performed on an upright light fluorescent microscope equipped with a fluorescein filter set (excitation 480/20 nm, emission 525/30 nm). Images were acquired at 30 Hz for several seconds using a CCD camera, and analyzed using ImageJ software. In our experiments, we detected the changes in intracellular calcium concentration that occur as a result of the generation of light-triggered action potentials in CMs (FIG. 6), and confirmed feasibility of all-optical assays that incorporates G-biointerfaces for light-controlled activation of cells.

Example 6: Biocompatibility of Neurons and G-Biointerfaces

Figure 7:
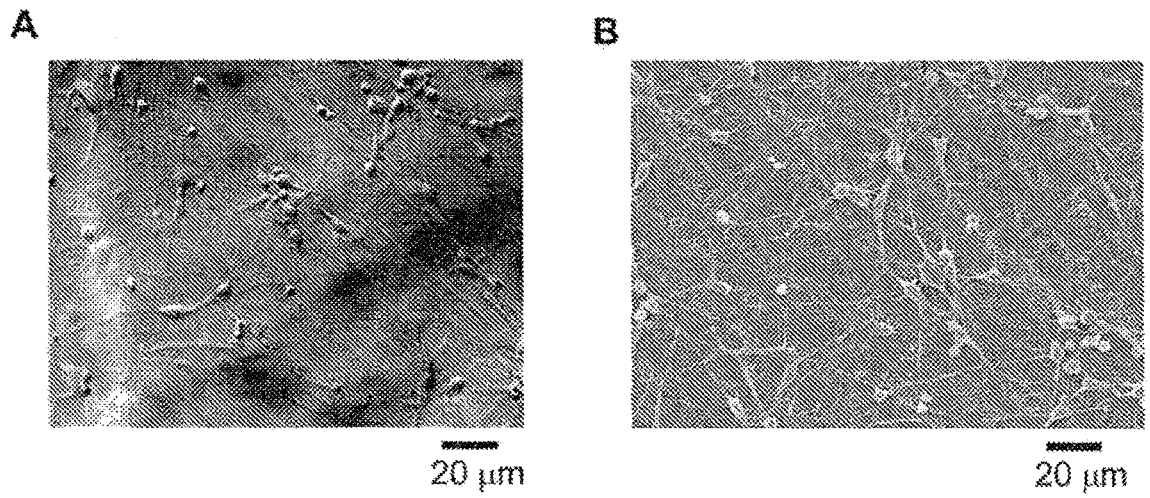
FIG. 7 shows the long-term culture of induced pluripotent stem cell (iPSC)-derived neurons that were plated on rGO-coated glass coverslips as represented by brightfield light microscopy images (A) and scanning electron microscopy images (B).

We evaluated the morphology of iPSC-derived neurons cultured on glass coverslips coated with graphene-related materials using both brightfield light microscopy and SEM (FIG. 7). We determined that iPSC-derived neurons did not change their morphology after being cultured on rGO-coated glass coverslips for 6 weeks.

Figure 8:
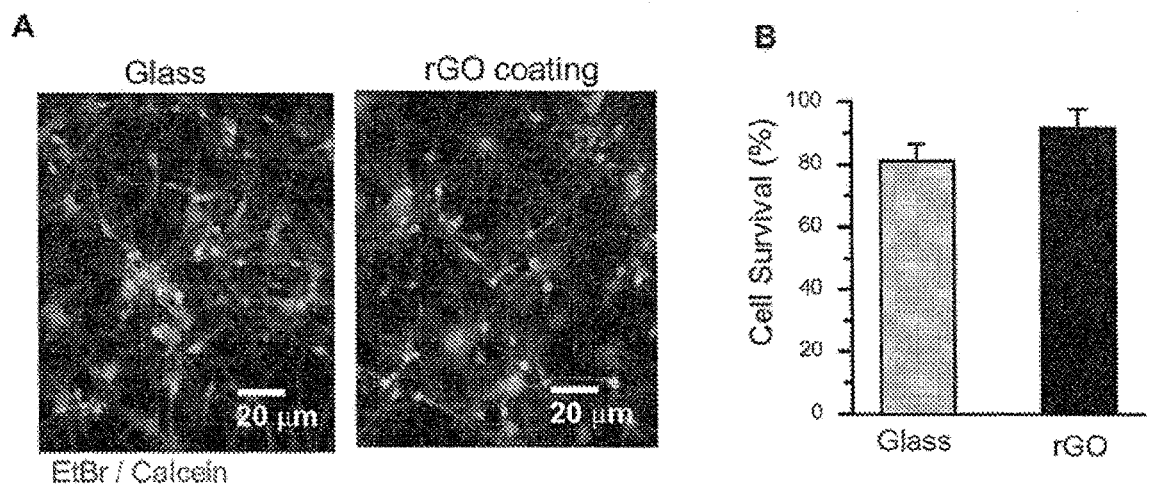
FIG. 8 shows excellent biocompatibility of rGO-coated glass coverslips for iPSC-derived neurons. (A) Neurons cultured on glass coverslips (left) and rGO-coated glass coverslips (right) were stained with Calcein-AM and EthD-1 to label live cells (green) and dead cells (red), respectively.

To assess biocompatibility of iPSC-derived neurons and rGO-coated glass coverslips, we performed viability experiments using the LIVE/DEAD® Viability/Cytotoxicity Kit (Life Technologies). We analyzed the results as described in Example 4 and determined that cell viability was higher on rGO-coated than on "naked' glass coverslips (FIG. 8).

Example 7: G-Biointerface and Light-Triggered Effects in Neurons

We performed the electrophysiological studies on iPSC-derived neurons according to the experimental protocol described in Example 5 ((FIG. 9A). We determined that, as in CMs, light illumination triggered membrane depolarization in neurons, leading to generation of action potentials (FIG. 9B).

To perform all-optical interrogation of neuronal activity, we activated neurons by illuminating their rGO-coated substrates with light and monitored their light-triggered activity using Fluo-4, a fluorescent calcium-sensitive indicator (FIG. 10A), as described in Example 6. We successfully recorded the changes in intracellular calcium during electrical activity triggered by light illumination only in neurons cultured on rGO-coated substrates (FIG. 10B).

Example 8: Statistical Analysis

Data were expressed as mean±s.e.m. When suitable, results were interpreted using a one-way ANOVA with a Student-Newman-Keuls (SNK) post-hoc test. Pairwise comparisons between genotypes/treatments were assessed with a Student's t-test. Differences were considered statistically significant at $P<0.05$.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A method of using an activating system to elicit changes in a functional state of at least one biological target, the method comprising:
   providing the activating system, the activating system comprising:
      at least one biointerface adapted to generate free charge carriers in response to exposure to electromagnetic radiation, the at least one biointerface comprising one or more materials comprising at least one graphene sheet, graphene oxide, reduced graphene oxide, graphite, graphite oxide, or combinations thereof;
      at least one source of electromagnetic radiation adapted to expose the at least one biointerface to the electromagnetic radiation; and
      the at least one biological target comprising live cells that contact or are positioned in sufficient proximity to the at least one biointerface such that cell membrane potentials of the live cells are remotely and reversibly manipulated by the free charge carriers generated by exposure of the at least one biointerface to the electromagnetic radiation;
   positioning the at least one biological target and the at least one biointerface; and
   exposing the at least one biointerface to the electromagnetic radiation from the at least one source of electromagnetic radiation, generating the free charge carriers, and remotely and reversibly manipulating the cell membrane potentials of the live cells.

2. The method of claim 1, wherein the live cells comprise one or more intact cells.

3. The method of claim 1, wherein said exposing the at least one biointerface to the electromagnetic radiation comprises exposing the at least one biointerface to visible spectrum electromagnetic radiation, radio frequency spectrum electromagnetic radiation, infrared electromagnetic radiation, microwave spectrum electromagnetic radiation, or combinations thereof.

4. The method of claim 1, wherein said exposing the at least one biointerface to the electromagnetic radiation comprises exposing the at least one biointerface to visible light.

5. The method of claim 1, wherein the live cells are selected from the group consisting of: stem cells, stem cell-derived cells, patient-specific cells, embryonic stem cells, adult stem cells, induced pluripotent stem cells (iPSCs), neurons, cardio myocytes (CMs), photoreceptors, fibroblasts, endothelial cells, pancreatic cells, muscle cells, secretory cells, adipose cells, mesenchymal stem cells, and bone forming stem cells.

6. The method of claim 1, wherein said exposing further comprises changing a membrane permeability of the live cells.

7. A method of using an activating system for performing a biological assay, the method comprising:
   eliciting changes in a functional state of at least one biological target, said eliciting changes comprising:
      providing the activating system, the activating system comprising:
         at least one biointerface adapted to generate free charge carriers in response to exposure to electromagnetic radiation, the at least one biointerface comprising one or more materials comprising at least one graphene sheet, graphene oxide, reduced graphene oxide, graphite, graphite oxide, or combinations thereof;
         at least one source of electromagnetic radiation adapted to expose the at least one biointerface to the electromagnetic radiation; and
         the at least one biological target comprising live cells that contact or are positioned in sufficient proximity to the at least one biointerface such that cell membrane potentials of the live cells are remotely and reversibly manipulated by the free charge carriers generated by exposure of the at least one biointerface to the electromagnetic radiation;
      positioning the at least one biological target and the at least one biointerface; and
      exposing the at least one biointerface to the electromagnetic radiation from the at least one source of electromagnetic radiation, generating the free charge carriers, and remotely and reversibly manipulating the cell membrane potentials of the live cells; and
   monitoring said changes in the at least one biological target using one or more detection methods.

8. The method of claim 7, wherein the monitoring of said changes in the at least one biological target is performed using optical detection methods.

9. The method of claim 7, wherein the monitoring of said changes in the at least one biological target comprises monitoring changes in the target's functional state, the changes comprising changes in one or more of: morphology, cell migration, cell viability, cell metabolism, intracellular ion concentrations, cell membrane potential, mitochondrial membrane potential, intra/extracellular concentrations of signaling molecules, enzymatic activity, translocation of intracellular molecules, or combinations thereof.

10. The method of claim 7, wherein the monitoring of said changes in the at least one biological target is performed using electrophysiological detection methods, comprising patch clamp techniques, planar electrophysiological systems, extracellular recordings, microelectrode arrays, field transistors, carbon nanotubes, or combinations thereof.

11. The method of claim 7, wherein the monitoring of said changes in the at least one biological target is performed using genetic detection methods, comprising polymerase chain reaction (PCR), reverse transcription PCR (RT-PCR), deoxyribonucleic acid (DNA) sequencing, next generation sequencing, DNA microarrays, karyotyping, fluorescence in situ hybridization, calorimetric in situ hybridization, or combinations thereof.

12. The method of claim 7, further comprising using the at least one biointerface for bidirectional communications with the at least one biological target by stimulating the at least one biological target and monitoring resultant changes in the at least one biological target using either imaging or electrical modality, or combinations thereof.

13. The method of claim 7, further comprising exposing the live cells to chemical entities, monitoring cellular responses of the live cells to the chemical entities, and screening, pharmacological profiling, and evaluation of the chemical entities in terms of their pharmacological properties, potential cardiotoxicity, neurotoxicity, metabolic toxicity, or combinations thereof.

14. The method of claim 7, further comprising exposing the live cells to chemical entities, monitoring cellular responses of the live cells to the chemical entities, and pharmacological profiling of the live cells, in terms of their membrane receptors, ion channels, transmembrane transporters, kinases, phosphatases, or combinations thereof.

* * * * *

UNITED STATES PATENT AND TRADEMARK OFFICE
CERTIFICATE OF CORRECTION

PATENT NO. : 10,688,127 B2
APPLICATION NO. : 16/129535
DATED : June 23, 2020
INVENTOR(S) : Elena Molokanova It is certified that error appears in the above-identified patent and that said Letters Patent is hereby corrected as shown below:

In the Specification

Column 3, Lines 50-51, delete "grapliene" and insert --graphene--.

Column 6, Line 39, delete "EchD-1" and insert --EthD-1--.

Signed and Sealed this
Twenty-second Day of September, 2020

Andrei Iancu
*Director of the United States Patent and Trademark Office*